United States Patent [19]
Ritsche

[11] Patent Number: 5,901,883
[45] Date of Patent: May 11, 1999

[54] DISPENSER HAVING NOZZLE INSERT WITH PASSAGES FOR DISCHARGE OF TWO MEDIA

[75] Inventor: Stefan Ritsche, Radolfzell, Germany

[73] Assignee: Ing. Erich Pfeiffer GmbH, Radolfzell, Germany

[21] Appl. No.: 08/741,240

[22] Filed: Oct. 30, 1996

[30] Foreign Application Priority Data

Nov. 8, 1995 [DE] Germany ................ 195 41 594

[51] Int. Cl.⁶ ................................................ B67D 5/52
[52] U.S. Cl. ............... 222/137; 222/145.1; 222/183; 222/321.9
[58] Field of Search .................... 222/135, 136, 222/137, 145.1, 145.3, 183, 321.7, 321.9

[56] References Cited

U.S. PATENT DOCUMENTS

| | | | |
|---|---|---|---|
| 3,549,052 | 12/1970 | Forim | 222/135 |
| 4,773,562 | 9/1988 | Gueret | 222/135 |
| 4,826,048 | 5/1989 | Skorka et al. | 222/137 |
| 4,880,143 | 11/1989 | Murray et al. | 222/135 |
| 4,902,281 | 2/1990 | Avoy | 604/191 |
| 4,949,874 | 8/1990 | Fiedler et al. | 222/135 |
| 4,989,597 | 2/1991 | Werner | 128/203.12 |
| 5,169,029 | 12/1992 | Behar et al. | 222/1 |
| 5,176,654 | 1/1993 | Schreiber | 604/181 |
| 5,224,627 | 7/1993 | Weag | 222/135 |
| 5,301,841 | 4/1994 | Fuchs | 222/135 |
| 5,332,157 | 7/1994 | Proctor | 239/304 |
| 5,337,738 | 8/1994 | Heinonen | 128/203.12 |
| 5,411,176 | 5/1995 | Favre | 222/94 |
| 5,611,463 | 3/1997 | Favre | 222/145.1 |
| 5,645,193 | 7/1997 | Gentile et al. | 222/137 |

FOREIGN PATENT DOCUMENTS

| | | |
|---|---|---|
| 0 299 757 A2 | 1/1989 | European Pat. Off. . |
| 0 427 609 A1 | 11/1990 | European Pat. Off. . |
| 0 486 894 A1 | 5/1992 | European Pat. Off. . |
| 0 692 312 A1 | 7/1995 | European Pat. Off. . |
| 2 641 337 | 1/1989 | France . |
| PS 8 08 613 | 7/1951 | Germany . |
| OS 14 57 439 | 2/1969 | Germany . |
| AS 19 23 049 | 9/1972 | Germany . |
| 33 45 630 A1 | 7/1984 | Germany . |
| 84 18 594 U1 | 11/1984 | Germany . |
| 91 02 463.3 | 6/1992 | Germany . |
| 41 06 575 C1 | 7/1992 | Germany . |
| 43 00 880 A1 | 7/1994 | Germany . |
| 35 25 449 C2 | 2/1995 | Germany . |
| 43 05 722 C2 | 8/1995 | Germany . |
| WO 89/08470 | 9/1989 | WIPO . |

Primary Examiner—Joseph A. Kaufman
Attorney, Agent, or Firm—Quarles & Brady LLP

[57] ABSTRACT

A discharge unit (1) contains two separate delivery units (15) to be actuated in common through which the medium flows along a module (35) separate from two base bodies (4,5) to two atomizer nozzles (48) so that due to their spray cones overlapping each other the two separately emerging media are intermingled in utmost fine dispersion and, e.g. with the formation of a gelling blended medium, react with each other. As a result of this two media reacting with each other chemically or physically can be intermingled not before being outside of the discharge nozzles (48) and thereby simultaneously applied to the region of application, e.g. a mucuous membrane.

25 Claims, 3 Drawing Sheets

DISPENSER HAVING NOZZLE INSERT WITH PASSAGES FOR DISCHARGE OF TWO MEDIA

TECHNICAL FIELD AND BACKGROUND OF THE INVENTION

The invention relates to a discharge unit for two media which may be flowable, for example, gaseous, liquid, pasty or gel-like and/or powdery, i.e. in each case before and after discharge from the unit.

The discharge unit may in each case comprise either individually, or in combination a housing body, a medium delivery unit, a discharge actuator, an outlet passage, a discharge orifice and, configured separately or integrally in the housing body, a module which may be an actuating plunger, an outlet valve or some other internal body or region capable of limiting the cross section of a discharge or outlet passage.

The discharge unit may comprise only one of two base bodies or actuator units, which are to be manually moved singlehandedly, rotatingly and/or axially with respect to each other to actuate the discharge so that this actuator unit is then to be connected to the further actuator unit, for example, by snap-mounting for use of the discharge unit. Preferably, however, both actuator units are preassembled and disposed with respect to each other so that their movement with respect to each other is still required for activating the discharge. One of the actuator units contains the discharge orifice and the other actuator unit the media reservoir, however, both actuator units or housing bodies could also be configured integrally.

Preferably, one housing body features at least one, and possibly two or more discharge orifices, of which at least one for releasing the medium from the discharge unit ports to the atmosphere, while one or more further discharge orifices may be located within the corresponding housing body in the direction of flow upstream of the aforementioned discharge orifice and may be aligned either along the same axis or may deviate from each other. If two media are required to be discharged separately, then two discharge orifices leading to the atmosphere are juxtaposed in at least one of the last-mentioned arrangements, so that the two media mix directly subsequent to emergence from the two discharge orifices and thus form a chemical and/or a physically reacting, blended media. If, for instance, the blended media, due to the reaction, are flowable to a lesser degree than one of the two starting media, due to these translating into a gel-like consistency as a result of molecular crosslinking during blending, then it is expedient to maintain these two media completely isolated until shortly before discharge into the atmosphere and not to bring them together until spaced away from the discharge surface of the discharge unit. In this arrangement a good mixing is achieved, especially when at least one of the media is introduced to the other as finely dispersed as possible.

OBJECTS OF THE INVENTION

The invention is embodied in a discharge unit in which the drawbacks of known configurations are avoided and/or the benefits or effects of the kind described herein are achieved. Further objects are the capability for good mixing of the separate media or, during delivery, enabling the media to be maintained in a flowable condition for as long as possible, simplifying the structure, and assembly of the unit and rendering the unit particularly suitable for application in bodily openings such as nasal openings.

SUMMARY OF THE INVENTION

In accordance with the invention, an internal discharge orifice and/or one leading to the atmosphere may be formed by an output of an atomizer nozzle from which the medium emerges very finely dispersed. If two media are passed through respective discharge orifices these can be blended very well using the present invention. This is even further improved where two or more such discharge orifices are each formed by a separate output of separate atomizer nozzles and where the atomization cones of these nozzles achieve interaction by large or major portions of their cross-sections a short distance after discharge from the discharge orifices.

Each atomizer nozzle preferably comprises a nozzle discharge orifice of less than one or a half millimeter width internally, a passage directly upstream of the orifice for swirling the medium concerned or for producing a vortex about the nozzle axis or including an internal body or nozzle core located directly upstream of the orifice, the latter being formed by a component separate from the wall through which the nozzle orifice passes. This internal body may also define, either alone or together with another component, an associated passage section of the outlet passage leading to the discharge orifice.

Preferably, two internal bodies associated with separate discharge orifices or outlet passages are integrally formed in a nozzle insert which can be secured to or further made integral with an associated base body. Alternatively, two connections for two separate discharge delivery units may be formed through one such module insert. In the case of a discharge unit having merely a single discharge orifice leading to the atmosphere or having merely a single discharge delivery means or media reservoir, this nozzle insert may contain only a single internal body and a single connector. Preferably, the nozzle insert comprises, at the end of the internal body or connector, a carrier part for securing to a housing body so that the nozzle insert can be preassembled with the housing body and then joined to the discharge delivery means or the like. Preferably, the nozzle insert is secured to the housing body by a bonding connection, such as welding, or via a self-latching or spring-type snap-connection, the snap-action members of which are to be interconnected in the same direction in which the internal body is to be inserted or the connection is to be made with the discharge delivery unit. The carrier part may define one or more longitudinal and/or transverse sections of the discharge passage which preferably pass full-length from the discharge orifice of the discharge delivery unit, without intervening valves to the discharge orifice.

The discharge orifices may pass through, in a common axial plane, a wall observed in an axial view as a flattened oval, an ellipse or a shape with a similarly elongated outermost circumference, the largest extension of which lies parallel to the straight lines connecting the discharge orifices. The limit of this wall thus forms areas of strong curvature opposing each other and, laterally thereto, areas of less curvature opposing each other. Counter to the direction of flow the outer circumference of the corresponding component, such as a discharge port adjoining the limit of this wall, translates into a shape in which the differences in curvature between the areas of curvature are less. For example, the outer circumference of this component at its end remote from the discharge orifice may be approximately circular. The orifice may have a diameter which corresponds to the further extension of the face of an end wall, so that the shape of the face of the end wall is achieved by a flattening of this circular or similar shape which in the axial direction is a continuous opposing surface. Such a configuration is advantageous for many applications having only a single or final discharge orifice leading to atmosphere.

Besides reversibly operating discharge devices which comprise at least one pump and at least one media reservoir charged by a pressurized propellant and actuated by opening a valve and by actuating a reciprocally moveable discharge head, the configurations according to the invention also include so-called disposable discharge devices in which the outlet passage directly connects to the media reservoir which forms the pumping or pressure space. In the case of a plunger pump, the plunger in this arrangement plunges into one end of the pressure space, at the inner circumference of which the plunger forms a seal and glides axially over a plunger lip. The end of the pressure space opposite the plunger may be closed after being emptied, and its refill with medium due to a return stroke is not provided for. Once the plunger has attained this opposite end of its one-way stroke, the complete media reservoir is substantially completely emptied.

These and further features are evident not only from the claims but also from the description and the drawings, each of the individual features being achieved by themselves or severally in the form of subcombinations in one embodiment of the invention and in other fields and may represent advantageous aspects as well as being patentable in their own right, for which protection is sought herein. It will be appreciated that dividing the application into separate sections as the use of headings does not restrict the reading or interpretation hereof.

BRIEF DESCRIPTION OF THE DRAWINGS

Example embodiments of the invention are explained in more detail in the following description and are illustrated in the drawings which form a part hereof and in which.

DETAILED DESCRIPTION

Figures 2, 5, 6, 7:
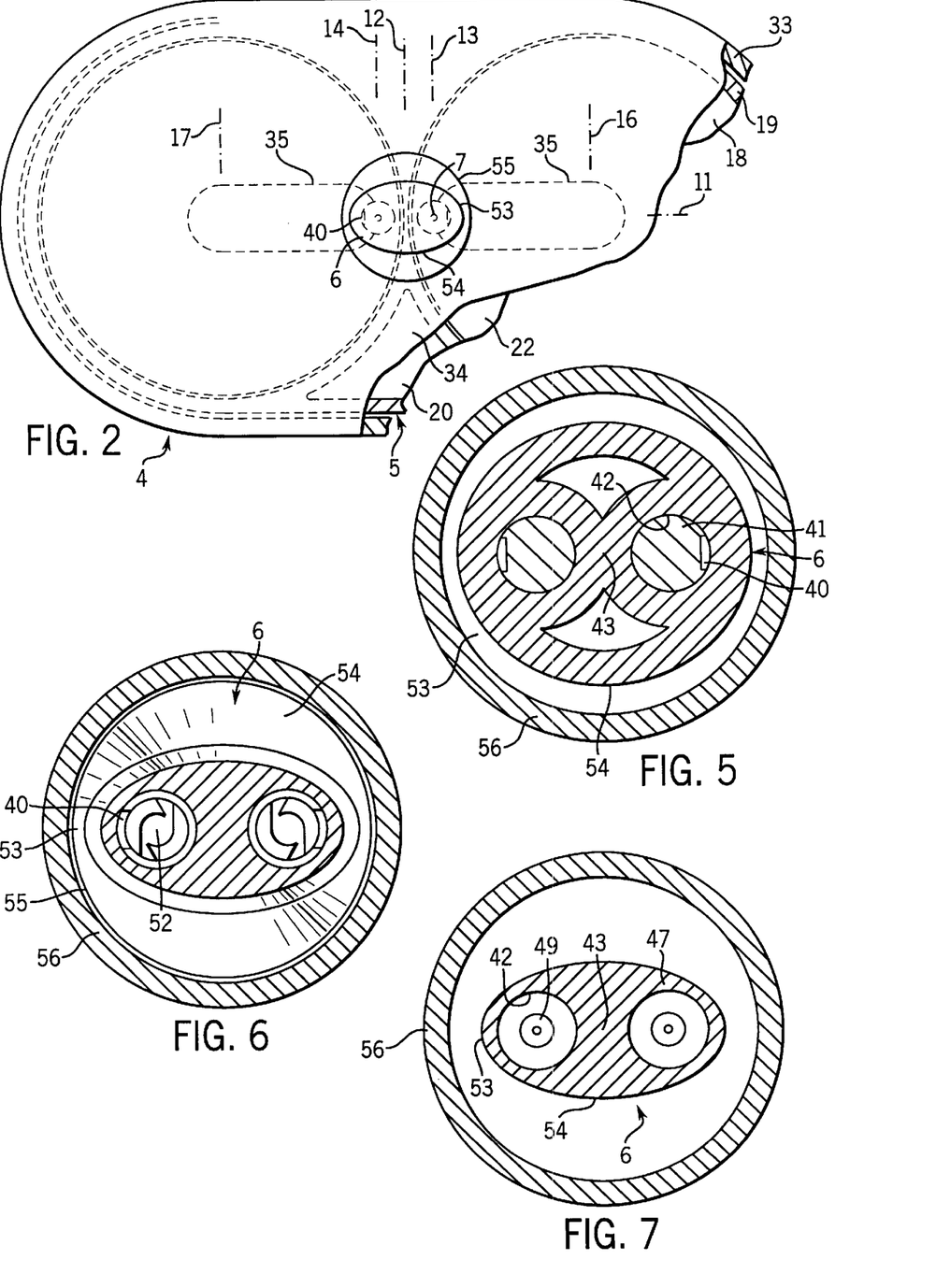
FIG. 2 is a plan view of the device of FIG. 1 in a slightly modified configuration.
FIG. 5 is a sectional view taken along the lines V—V in FIG. 4.
FIG. 6 is a sectional view taken along the lines VI—VI in FIG. 4.
FIG. 7 is a sectional view taken along the lines VII—VII in FIG. 4.
Figure 3:
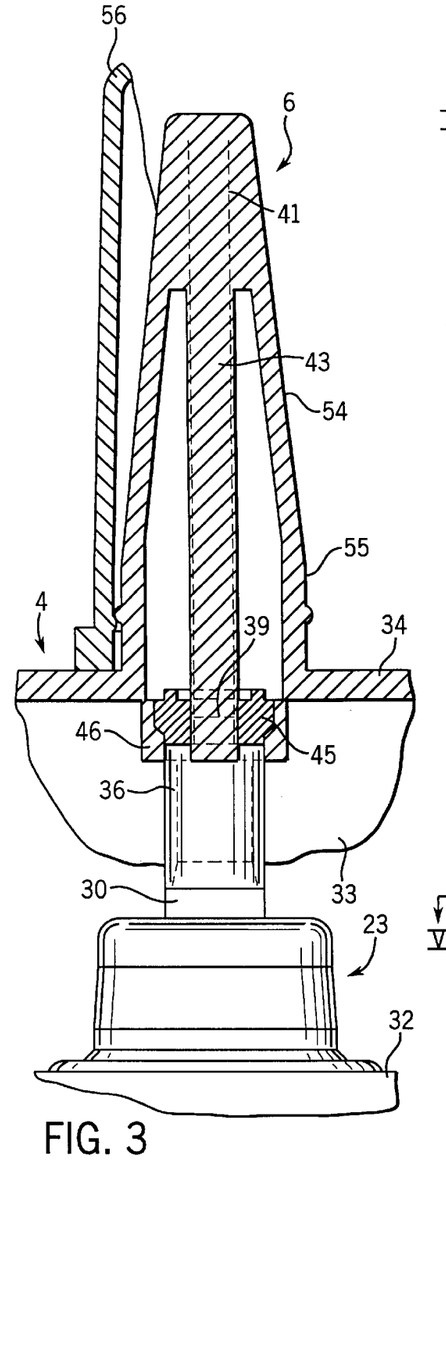
FIG. 3 is a partial sectional view taken through the device of FIG. 1 and represented on a magnified scale.
Figure 4:
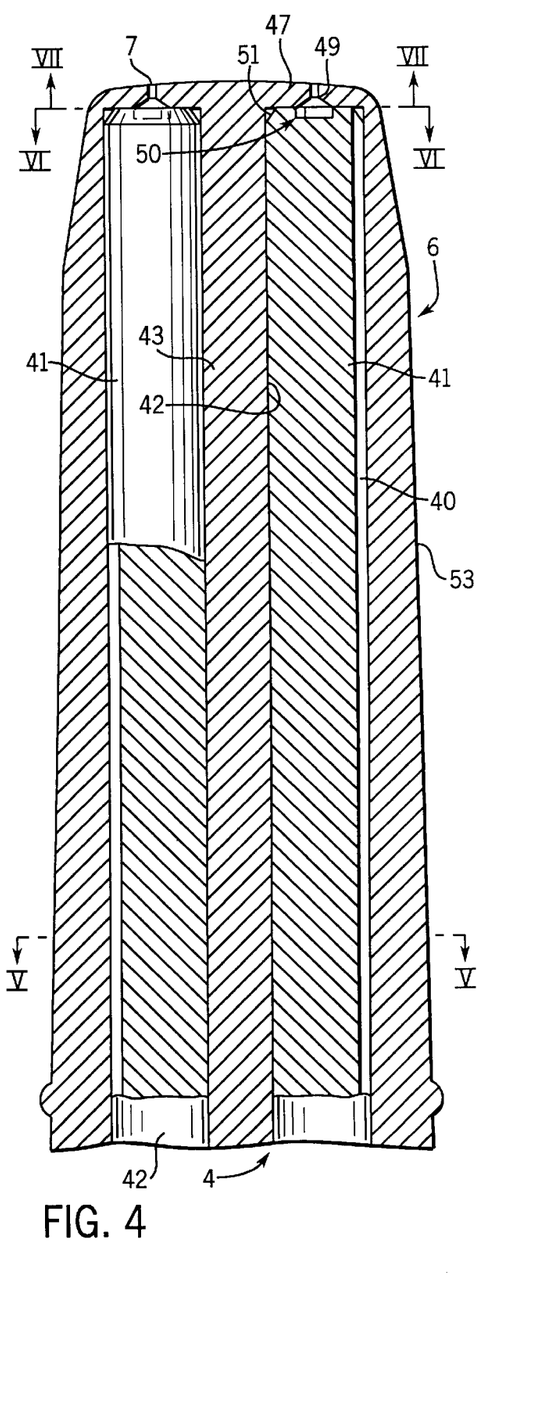
FIG. 4 is a cut-out section of the device FIG. 1 represented on substantially magnified scale.

In accordance with the invention units 1 to 3 are provided for discharging two media the actuator units 2, 3 are assembled together in the discharge unit 1 for moving with respect to each other by the pressure of the fingers of one hand only, while freely carrying the unit 1 and by operation over a maximum stroke of less than 10 or 5 mm. Each unit 2, 3 comprises a separate, housing body 4 and a lower housing 5 of plastic material, which when viewed axially, have approximately the same oval shape. The longer housing body 4 encloses, protruding freely past its outside surface, a nozzle body 6 having one or more discharge orifices 7 emerging in an axial direction at its free end. On a top surface, the body 4 forms finger grips 8 or finger pressure surfaces adjoining the sides of the nozzle body 6. An opposing grip 9 is formed by the housing body 5 on its bottom end. The components 1 to 9 are located substantially axially parallel or symmetrical about a longitudinal center line 10, defining an axis with center planes 11, 12 passing through the axis 10 at right angles to each other. The components 1 to 6, 8 and 9 extend at least 1.5 and maximally 3 times wider in the direction of the middle plane 11 than in the direction of the plane 12. Two axial planes 13, 14 passing through the discharge orifices 7 are symmetrically disposed on both sides of the plane 12 and are parallel thereto. Each discharge orifice 7 is supplied with medium by a separate delivery unit 15, 15' and the axes parallel to axis 10 or the axial planes 16, 17 parallel to the planes 12 to 14 of two medium dispensing and reservoir units 15, 15' are located symmetrically on both sides of the plane 12 in a spacing which is several times greater than the spacing of the planes 13, 14 so that they are provided far away from the nozzle body 6 in accordance with FIG. 2.

The housing bodies 4, 5 form in common a housing which is closed to the outside and flatly oval in the axial view in which the medium dispensing and reservoir units 15, 15' are totally enclosed and concealed. The units 15, 15' are rigidly and positively located by the shape and/or force on the housing body 5, which forms separate supports in the housing. The housing body 5 comprises a radial outermost shell 19 which is roughly as long as it is wide and which is closed off at one end by a end wall 20 and the other end being open for inserting or linearly inserting the units 15, 15'. The shell 19 is subdivided by a partition 21 located symmetrically to the plane 12 in the two cylindrical receiving pockets 18. These are cylindrically adapted to bottle-like media reservoirs 22 of the units 15, 15' such that one reservoir 22 each in a support 18 is secured against withdrawal by a circumferential clamp or snap spring retainer when its bottom comes up against the inner side of the end wall 20, the reservoirs 22 being totally located within the units 15, 15'. Freely protruding from a reservoir orifice formed by a constricted neck section is a medium delivery means 23 like a plunger pump. To form the unit 15, the medium delivery means 23 is inserted coaxially as a preassembled delivery unit into the reservoir 22. The widened belly of reservoir 22 is configured integrally with a neck of glass or the like. The delivery means 23 comprises an elongated delivery housing 24 which is made up of a cylindrical housing protruding into the reservoir belly and a housing cover 22a located outside of the reservoir 22. Within the cylindrical housing and the neck of the reservoir 22 a pumping or pressure space 25 is defined, the volume of which can be manually changed by an axially slidable plunger unit 26.

Through a ported inlet 27, medium is suctioned from the reservoir 22 into the pressure space 25 on the return stroke of the unit 26 via an inlet valve 28 operating as a function of pressure. Where a pumping stroke is effected between surface 8 and the grip 9, the medium is forced out of the pressure space 25 via an outlet valve 29. The valve 29 opens and closes as a function of pressure and/or travel respectively through a discharge passage 31 of an actuating plunger 30. The actuating plunger 30 is formed by the end of the plunger of the unit 26 slidably passing through the housing cover. The housing 24 is secured, rigidly located and axially tensioned to an outer collar of the reservoir neck by a fastener 32, which includes an outwardly located crimp ring so that the reservoir orifice is closed off by a seal surrounding the housing 24. This seal engages between the faces of the outer collars of the neck and the housing 24 and is located within the fastener 32 clasping the outer collars.

The housing body 4 closes the housing body 5 like a cap and at an open end contains, freely protruding in opposition to the shell 19, an outermost shell 33 which at one end facing away from the end wall 20 forms an oppositely facing end wall 34. The outer sides of the plates or end walls 34, 20 are located transversely or at right angles to the axis 10 and to the planes 11 to 17 to form the grips 8, 9, each of which extends only up to the outer circumference of the associated shell 33 or 19. The inner circumference of the shell 33 is approximately the same as the outer circumference of the shell 19, except for a small transverse gap which allows shell 33 to slide relative to shell 19, although the shell 19 could clasp the shell 33. The protruding parts of the units 15, 15' project into the shell 33. The components 23 to 32 of each unit 15, 15' lie in the associated axis or plane 16, 17. Both reservoirs 22 extend directly up to the thin partition 21 so that their clearance corresponds to the minimum thickness of this wall 21.

The housing body 4 carries an axially insertable and firmly secured nozzle insert 35 which is located totally concealed within the body 4 or by the cap 56 or by nozzle body 6. The housing body 4 is dimensionally and/or forcibly positively secured in each case by a sleeve-shaped connector 36 freely projecting from the inner side of its face end wall 34 to the associated plunger 30 configured integral with the dimensionally rigid nozzle insert 35 of plastics material from which it protrudes freely to the grip 9. The outer circumference of the plunger 30 sealingly engages the connector 36 or the inner circumference thereof. The connector 36 is also in contact through its end surface with a shoulder of the plunger 30.

The discharge orifice of each discharge passage 31 located in the end surface of the plunger 30 is always conductively connected to the corresponding discharge orifice 7 without intervening valves via a separate outlet passage 37. The multiply angled outlet passage 37 is formed within the connector 36 and includes a first longitudinal section 38 which adjoins the discharge passage 31 in the direction of flow at one end. The outlet passage 37 also includes a transverse section 39 which adjoins the longitudinal section 30 at one end and which adjoins in the direction of flow at the other end a longitudinal section 40 which is substantially constricted with respect to both sections 38, 39. The transverse section 39 lies on the inner side of the end wall 34 and is defined circumferentially and totally closed in cross section by the latter and by the nozzle insert 35. The nozzle insert 35 is for this purpose provided with separate grooves at its side adjoining the end wall 34 so that the section 39 is oriented from section 38 or the plane 16 and 17 to the axis 10 or the planes 12 to 14 transversely or at right angles thereto in a straight line throughout. Both sections 39 coincide. The sections 40 parallel to the axis 10 and to the planes 11 to 17 pass through the nozzle body 6 on sides of the planes 12 to 14 facing away from each other and also lie in the plane 11. They pass with a constant flow cross-section from each section 39 approximately up to the discharge orifice 7 or to an associated swirler 50 and connect directly the end of the corresponding section 39 in each case. The length of the nozzle body 6 is several times greater than its smallest or largest outer width.

Each passage section 40 is located within a separate drilled passage-like support 42 which passes through the end wall 34 and the nozzle body 6 approximately up to the free end thereof with constant width and supports a rod-shaped, for example, cylindrical internal body 41 closely fitted or by means of a circumferential clamping fit. The two supports 42 located n the planes 13, 14 are sealed off from each other by a partition of the housing body 4 and nozzle body 6 respectively, this partition protruding from the free end of the nozzle body 6 up to the other end thereof and past the inner side of the end wall 34. The thickness of the partition 43 roughly equals the wall or shell thickness of the elements 4 to 6 and at their sides facing away from each other the internal bodies 41 adjoin so that the sections 40 locate at the shell sides of the internal bodies 41 facing away from each other. Each internal body 41 protrudes by its inner end 44 facing away from the discharge orifice 7 past the inner side of the end wall 34, forming the corresponding end definition of the section 39 and adjoining the nozzle insert 35 integrally.

The nozzle insert 35 encompasses a plate-shaped elongated carrier part 45 located transversely or at right-angles to the axis 10 or the planes 11 to 17 parallel to the plane 11, the inner end 44 of each of the straight-line internal bodies 41 integrally adjoining directly adjacent to the partition 43, so that it only protrudes past one plate side. Offset outwardly only past the plate side facing away therefrom and radially with respect to the internal bodies 41 the connections 36 protrude axially parallel to each other and to the internal bodies 41. The carrier part 45 defines the passage sections 39 and the inner ends of the passage sections 40, the edge of which also extends over the free outer circumference of the connections 36 as a bead 45a.

Only the carrier part 45 of the nozzle insert 35 is retained by its edge full-length continuously over the bead 45a to a fastener 46 at the inner side of the face end wall 34. The housing body 4 forms a sleeve protruding past the inner side of the end wall 34 or a collar 46, in the inner circumference of which the edge of the nozzle insert 35, 45 is locked with zero clearance against axial, radial and rotary movements and in which it sealingly engages. The inner circumference of the fastener 46 and the outer circumference of the carrier part 45 or of the connections 36 forms sealingly interacting locking or snap-action members 45a, 46 which following the pliant expansion of the fastener 46 latch into place when the nozzle insert 35 is inserted with the internal bodies 41 coming up against the inner side of the end wall 34 at the end of axial insertion movement. This results in the ends of the sections 38, as well as the corresponding open groove longitudinal sides of the sections 39, being sealingly closed by this inner side. The carrier part 45 and the inner side of the end wall 34 may comprise, on sides facing each other along the edge of the carrier part 45, one or more ring-shaped continuous full-length protrusions 45a, each of which sealing engages in a corresponding groove recess of the other component and thus forms a labyrinth seal. Each connection 36 or internal body 41 could, in accordance with FIG. 2, comprise a separate carrier part or be formed by a separate unit 35, it being expedient, however, to provide a common integral unit 35 for both units 15, 15' or both discharge orifices 7.

Each passage section 40 is located over the full length of the associated internal body 41 on the outer circumference thereof which is provided with a corresponding longitudinal groove so that the section 40 is closed cross-sectionally over the circumference by the outer circumference of the internal body 41 and the inner circumference of the support 42. The groove extends up to the corresponding side of the carrier part 45, up to the inner end of the internal body 41 and up to the bottom surface of the transverse groove 39. The nozzle body 6 comprises, radially spaced by one or two inner shells, an outermost supporting shell, the inner end of which adjoins integrally the end wall 34 and the outer end of which integrally translates into a end wall 47 at a right angle to the center line 10 and the planes 11 to 14, 16, 17 passing through by one of the discharge orifices 7.

Together with the outer ends 51 of the internal bodies 41 this end wall 47 forms atomizer nozzles 48, the nozzle outlets of which directly form the respective discharge orifices 7, through which the medium is fully liberated from the medium dispenser 1 on each discharge. The discharge orifice 7 is formed by the outer end of a nozzle passage 49 passing through the end wall 47, the inner end of this passage may be conically flared and connected via a swirler or vortex means 50 to the end of the corresponding section 40. This swirler means 50 is expediently located between the inner surface of the end wall 47 and facing end surface of the corresponding internal body 41 which in accordance with FIG. 6 may feature at its outer circumference adjoining recessed swirl passageways 52. The swirl passageway 52 of the means 50 in each case may form at the center about the nozzle axis a rotation chamber to which two or more radial or tangential passages adjoin from the outer circumference of the internal body 41 and from the inner circumference of the support 42, respectively. Preferably, the outer circumference of the end 51 is provided with a slanting surface or chamfer at which the tangential passages adjoin each other transversely to the plane 11 diametrically opposed outside of the section 40 so that along this chamfer an annular passage adjoining the end of the section 40 is formed. The medium conveyed through the section 40 flows from the end thereof initially in opposite directions into the annular passage and then from there firstly into the tangential passages and finally into the rotation chambers from which it gains access directly as a vortex flow to the nozzle passage 49 and escapes from the discharge orifice 7. In the annular passage and the means 50 the direction of flow of the medium is oriented transversely or at a right angle to the direction of flow in the section 40 and in the nozzle passage 49, respectively.

The outer end of the nozzle body 6 or the end wall 47, when viewed axially, is at the outer circumference parallel to the plane 11 elongated flatly-oval or elliptically, whereby the axes of the discharge orifices 7 in the axes of the minor circles of this ellipse or opposite thereto may be located slightly offset from the plane 12. As a result of this, the outer circumference of the nozzle body 6 forms over the circumference two regions 53 of more pronounced curvature opposing each other and transversely thereto two regions 54 of less curvature opposing each other, whereby both regions 53, on the one hand, as well as both regions 54, on the other, have the same curvature and each extend into the other continuously or smoothly tangentially. The inner end of the outer circumference of the nozzle body 6 adjoining the face end wall 34 is by contrast circular or consistently polygonal, the width of which being slightly greater than the greatest width between the regions 53 or substantially greater than the smallest width between the regions 54 at the outer port end. The regions 53, 54 extend from the port end continuously, conically and smoothly into the foot circumference 55 of the inner port end with constant curvature so that the elliptical cross-sectional shape at the free port end in the direction of the port foot continuously approximates the shape 55 of this foot with counter accommodation of the curvature of the regions 53, 54. At the free end section of the nozzle body 6 the conicity of the regions 53 is somewhat more pronounced than the regions 54.

Figure 1:
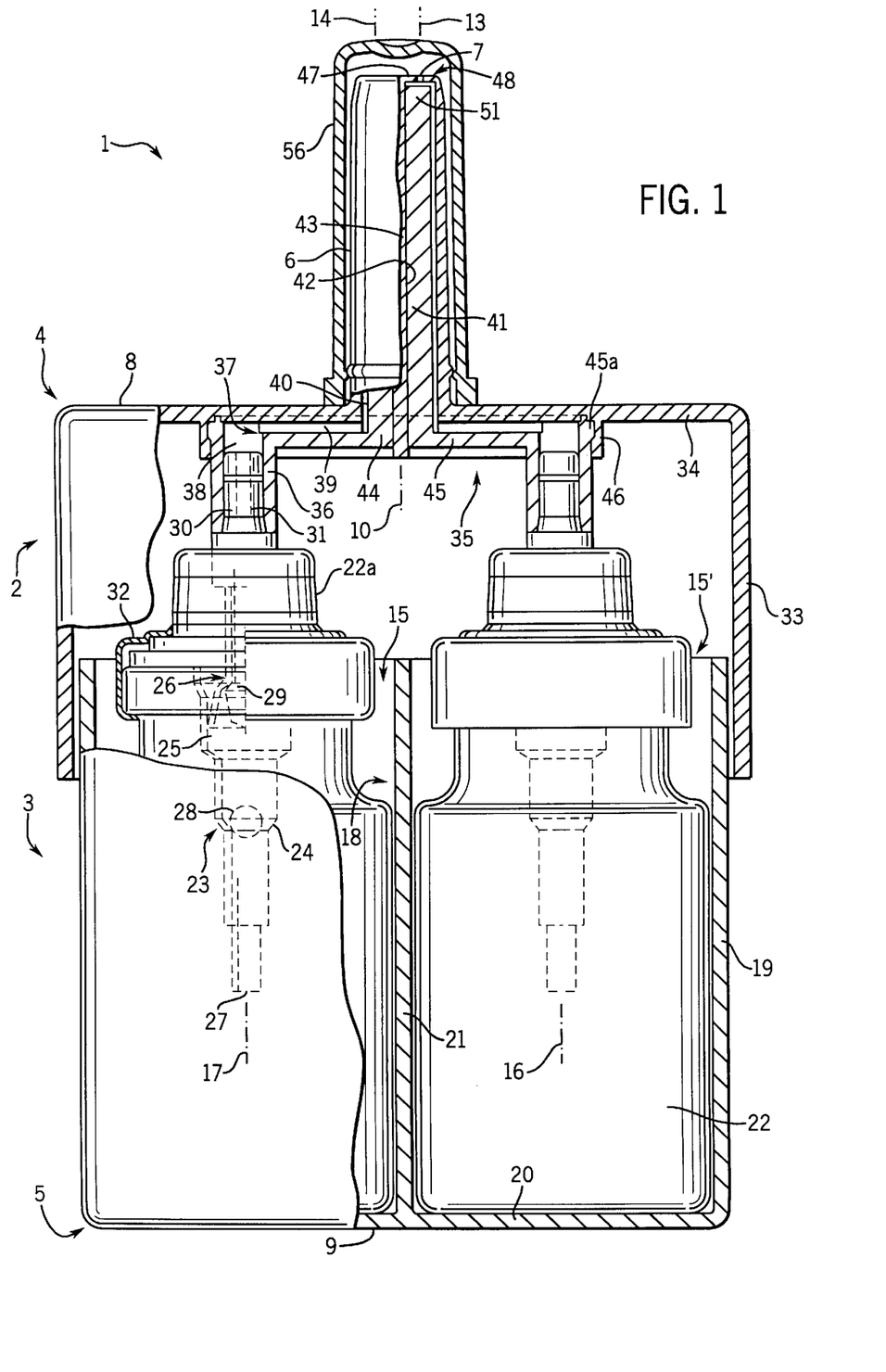
FIG. 1 is a partly sectioned view of a discharge unit according to the invention.

To discharge medium the dispenser 1 is held in one hand so that the thumb is in contact with the grip 9 and two other fingers with the grips 8 opposite each other. Against the force of return springs located within the two housings 24 or chambers 25 which at the same time may also be closing springs of the valves 28, 29, the two units 2, 3 are then pressed together, the body 5 plunging further into the housing body 4 and, where necessary, the connections 36 into the housings 24 extend as far as they will go. The housing body 4 thereby couples into its movement, exclusively via the connections 36, the two plunger units 26 of the two delivery units 15 15' with respect to the remaining components 22, 24, 32 and the housing body 5 at the same time or with a delay in time or travel so that both pressure spaces 25 are constricted by the plungers or displacement elements. As a result of this, the media contained in the pressure spaces 25 are subjected to pressure, causing the valves 28 to be maintained closed. After part of the pumping stroke or at the end thereof the outlet valves 29 open simultaneously or delayed in time with respect to each other, as a result of which the media are forced from the pressure spaces 25 through the plunger units 26 into the passage sections 38. From here they gain access, while being transversely deflected, directly to the passage sections 39 and again with an opposed deflection to the passage sections 40, until they emerge in the way as described from the discharge orifices 7 as an acutely or obtusely angled spray cone. The two jets or spray cones mix a short distance outside of the end wall 47 and form a blending zone in which the utmostly finely dispersed particles of the two media components emerging from the orifices 7 blend quickly and consistently. By suitably selecting the components this blending action of the inherently thin media results in the media reacting, such as gelling, with the blended medium then being substantially thicker, for example, so thick that its corresponding utmostly finely dispersed discharge from a nozzle in keeping with the nozzles 48 would not be possible. The furnished blended medium may nevertheless retain its utmostly finely dispersed condition or it may exhibit a delay in reaction so that the cited reaction does not come about until the spray jets impinge on a surface, for example, the mucous membrane of the nose. Following the precisely metered emergence of the media, loading of the grips 8, 9 is relieved, as a result of which the cited return springs alone return the units 2, 3 together with the medium delivery units 23 back into their starting position as shown in FIG. 1, so that a separate return spring directly urging the components 4, 5, 35 is not necessary. In this return stroke, medium is again suctioned from the reservoirs 22 into the pressure spaces 25. After return to the starting position, the dispenser 1 is instantly able to be actuated again in the way described for a further discharge.

In the case of a dispenser having only a single discharge orifice, only a single outlet passage or only a single medium delivery and reservoir unit 15 these embodiments could lie an the axis 10, so that also the components 36, 41 could be disposed along the same axis. In this case, namely when only a single internal body 41 or a single support 42 exists, the partition 43 would not be needed as in the depicted embodiment where the partition 43 integrally adjoins the inner circumference of the fastener 46 and extends up to the free end of the latter.

In the case of a so-called disposable dispenser, the internal body 48 or the nozzle insert 35 or the sleeve or connector 36 could directly carry the displacement element(s) or plunger (s) or form these integrally, and this plunger would then glide directly on the inner circumference of the reservoir(s) 42 so that the reservoir space thereof simultaneously forms the pressure space. The reservoir in each case could then be configured integrally with the body 5. Furthermore, freely protruding past the inner side of the end wall 34, radially outside of the inner circumference of the nozzle insert 6 a sleeve of the housing body 4 could be provided and guided radially outside of the reservoir space by the outer circumference of the shell thereof or by a shell of the housing body 5 spacingly surrounding the latter. In the starting position and/or in at least one further working position these shells could interengage via a latching or snap-action connection which is to be unlatched by a mutual rotary movement of the units 2, 3 and/or by applying a sufficiently strong compressive force to the grips 8, 9. Thus, for instance, the pretensioning force for overcoming this latching effect may result in an abrupt, strong pumping movement being initiated very quickly. The grip 8 or the end wall 34 and/or the grip 9 or the end wall 20 may also each protrude past the outer circumference of the corresponding shell 33 or 19 as an annular collar or in the shape of strip, so that especially in this case the cited latching action may be provided directly between the shells 19, 33.

In addition, the housing body 5 may comprise an outer shell which surrounds the shell 33 at the outer circumference in at least one or all operating positions. Furthermore, the internal body 41 may be secured to an inner shell of the body 4 protruding from the end wall 47 with radial spacing within the outer shell or contain, for instance, a hollow needle of steel or the like or be formed completely thereby. The reservoir or pressure space would then be sealingly closed off by the plunger and in the starting position the tip of the needle would directly oppose a design penetration point through this plunger. At the start of the pumping stroke the needle would then pass through the plunger and thus then adjoin the outlet passage located within and/or without of the needle to the pressure surface, by which in the further course of the stroke the plunger is included in the movement by a stop on a shoulder of the internal body and the medium ejected.

The outlet valve may also be formed by a peristaltic valve, the one valve seat of which is formed by the outer circumference of the internal body 41 and the other valve seat of which, movable with respect to the latter, is formed by the inner circumference of a cuff of the plunger through which the internal body passes. Instead of or in addition to this, the valve seats may also be formed by face ends of the internal body and of the plunger shiftable with respect thereto against the force of a valve spring and, for example, may be located at the front or inner end of the plunger. Furthermore, in the starting position or at the end of the pumping stroke the, housing body 5 or the reservoir 22 may protrude into the nozzle body 6. Between the bodies 4, 5 or 4, 22 or 4, 26 a positively acting safeguard against the bodies being pulled out or away from each other may be provided for effect by shape and/or force which, as may be required, e.g. like a bayonet-lock fitting is releasable by a rotary movement. Instead, the shell in each case or merely shell sections may be provided and distributed about the circumference and spaced away from each other with an appropriate large spacing to form freely projecting arms, the one being prevented from turning with respect to the other by the described shape of the two bodies 4, 5 or of the shells 33, 19.

The orifices 7 are closable by a cap-shaped closure 56, the open end surface of which in the closing position adjoins the face of end wall 34 between the grips 8 and which engages the outer circumference of the foot of the port 6 and is locked as a function of force via a snap connection. The inner circumference of the shell of the closure 56 is circular or consistently polygonal over its full length, the closure 56 shielding the complete port 6 and having at least dust-tight. The two delivery units 15, 15' may be configured identical or differently.

The invention may be practiced in embodiments in which various details may be provided precisely or merely substantially as explained above, and, where necessary, may depart greatly therefrom. Furthermore, each arrangement and each component may be provided only in a single, dual or multiple arrangement.

I claim:

1. A dispenser for discharging media comprising:

a housing (4,5) including a housing body (4);

at least one medium delivery means (23) connected with said housing (4,5);

said medium delivery means (23) including a moveable discharge actuator (30);

a nozzle body (6) projecting from said housing (4, 5), said nozzle body (6) being traversed by first and second nozzle ducts (49) including first and second discharge orifices (7) that allow media dispensed through said first and second discharge orifices (7) to separately release from said dispenser (1) at said first and second discharge orifices (7), each of said first and second nozzle ducts (49) respectively including an upstream end and a downstream end providing a respective one of said discharge orifices (7);

a nozzle insert (35) extending within said nozzle body (6) and together with said nozzle body (6) providing a longitudinally extending passageway (40) communicating between said delivery means (23) and said first nozzle duct (49); and wherein said nozzle insert (35) also includes a carrier (45) which encloses at least part of an outlet duct (37) communicating between said medium delivery means (23) and said longitudinally extending passageway (40), said nozzle insert (35) further including an end section (51) directly closely opposing and traversing said upstream end of said first nozzle duct (49), said first nozzle duct (49) being linear and circumferentially bounded in one part.

2. The dispenser according to claim 1, wherein at least one of said discharge orifices (7) communicates with said passageway (40) through a swirl passageway (52) formed between said longitudinally extending passageway (40) and an interior of said nozzle body (6).

3. The dispenser according to claim 1, wherein said first and second discharge orifices (7) are oriented in parallel discharge directions and are closely juxtaposed.

4. The dispenser according to claim 1, wherein means are provided for blending the media substantially exclusively downstream of said at least two discharge orifices (7), said blending means and said at least two discharge orifices (7) including outlets for at least one of two separate passageways (40) in said nozzle body (6), two swirl passageways (52) for swirling the medium prior to discharge from said discharge orifices (7), and two separate outlet ducts (37).

5. The dispenser according to claim 1, wherein said nozzle insert (35) also provides an interior carrier member (45) which encloses at least two separate outlet ducts (37) said outlet ducts (37) being commonly bounded by at least one internal body (41) partly forming said nozzle insert (35) and being inserted in at least one reception opening (42).

6. The dispenser according to claim 5, wherein said nozzle insert (35) includes at least two internal bodies (41), said internal bodies (41) being located in separate reception openings (42).

7. The dispenser according to claim 6, wherein said nozzle insert (35) includes juxtaposed body ends (44), said internal bodies (41) being inserted in said separate reception openings (42), said internal bodies (41) being directly interconnected by said nozzle insert (35) exclusively in the vicinity of said juxtaposed body ends (44).

8. The dispenser according to claim 1, wherein said nozzle insert (35) includes at least one internal body (41) including an end section (51) at one end proximate the discharge port (7) and bounding at least one of said outlet ducts (37) at on opposite end, said internal body (41) including an outer circumference and an end (44) proximate said carrier (45), said carrier (45) having a periphery on which one part (45a) of a snap-action securing connection (45a, 46) is formed.

9. The dispenser according to claim 8, wherein said nozzle insert (35) includes separate internal bodies (41) oriented parallel and directly juxtaposed, said internal bodies (41) separately projecting from said one part (45a) of said snap-action securing connection (45a, 46) and being made in one part with said internal bodies (41).

10. The dispenser according to claim 2, wherein said housing (4, 5) includes a first housing body (4) and a second housing body (5) displaceable with respect to said first housing body (4) to operate said discharge actuator (30), a mounting unit being provided and including said first housing body (4) and said nozzle insert (35), said nozzle insert (35) including a duct connector (36) for connecting said mounting unit with said medium delivery means (23) when preassembled to constitute a medium dispensing and reservoir unit (15) including at least one pressure chamber (25) for the medium, said first housing body (4) including a pressure face (8) for manually actuating said discharge actuator (30).

11. The dispenser according to claim 10, wherein said duct connector (36) directly connects to an actuating member (30), said actuating member (30) being manually displaceable with respect to at least one of said pressure chamber (25) for conveying the medium out of said pressure chamber (25), said duct connector (36) and said end section (51) being made in one part with said nozzle insert (35).

12. The dispenser according to claim 1, wherein said nozzle insert (35) includes an internal body (41) and a duct connector (36) oriented substantially parallel to said internal body (41) and laterally offset with respect to said internal body (41), said duct connector (36) having a free connector end and said internal body (41) having a downstream end section remote from said connector end, said internal body (41) longitudinally bounding said at least one outlet duct (37), said duct connector (36) being positioned to move an actuating member (30) for actuating said medium delivery means (23).

13. The dispenser according to claim 8, wherein said carrier (45) includes oppositely facing first and second support faces, at least one of said internal bodies (41) protruding from said first support face and at least one duct connector (36) protruding substantially exclusively over said second support face, said duct connector (36) being positioned to move an actuating member for actuating said medium delivery means (23).

14. The dispenser according to claim 13, wherein said carrier (45) is a planar member oriented transverse to at least one of said internal body (41), and said duct connector (36).

15. The dispenser according to claim 13, wherein said housing body (4) includes a peripheral wall (34) having an inside surface, said support member (45) being fixed directly to said inside surface and being entirely located within the peripheral wall of said housing body (4).

16. The dispenser according to claim 1, wherein said outlet duct (37) includes first, second and third duct sections (38, 39, 40), said first duct section (38) being located upstream of said second and third duct section (39, 40) and directly connecting to said second duct section (39), said second duct section (39) being oriented transverse to at least one of said first and third duct sections (38, 40), said nozzle insert (35) bounding said first, second and third duct sections (38, 39, 40), said second duct section (39) directly connecting to said third duct section (40) located downstream of said first and second duct sections (38, 39), in transverse cross-section at least one of said second and third duct section (39, 40) being circumferentially only partly bounded by said nozzle insert (35).

17. The dispenser according to claim 16, wherein said first and third duct sections (38, 40) are substantially parallel, said second duct section (39) being oriented transverse to said first and third duct sections (38, 40), in said cross-section at least one of said duct sections (38, 39, 40) being circumferentially only partly bounded by said housing body (4).

18. The dispenser according to claim 1, wherein said housing (4,5) includes a first housing body (4) and a second housing body (5), said first housing body (4) including a nozzle body (6) and pressure faces (8) for manually actuating discharge of the media, said pressure faces (8) freely radially projecting over remote circumferential sides of said nozzle body (6) traversed by said nozzle duct (49), said nozzle body (6) transversely projecting over said pressure faces (8) in a first direction oriented counter to a second direction, said first housing body (4) including a cap jacket (33) projecting from said pressure faces (8) in said second direction, said pressure faces (8) being defined by a cap end wall (34), said cap jacket (33) and said cap end wall (34) defining an actuating cap, within said actuating cap said nozzle insert (35) being rigidly connected to said first housing body (4), said nozzle insert (35) extending in said first direction beyond said pressure faces (8), for actuating at least one of said medium dispending means (23) via said pressure faces(8) substantially exclusively said nozzle insert (35) connecting said pressure faces with said medium dispensing means (23), wherein said nozzle body (6) is adapted for insertion in a human body opening.

19. The dispenser according to claim 18, wherein said second housing body (5) includes at least one medium reservoir (22), at least one of said medium delivery means (23) including first and second actuating units (24, 26) reciprocally displaceable for actuating discharge of the medium out of said medium delivery means (23) and into said nozzle insert (35), at least one of said medium reservoir (22) and said first and second actuating units (24, 26) together being included in a preassembled medium dispensing and reservoir unit (15) for assembling with said first housing body (4) and said nozzle insert (35).

20. The dispenser according to claim 19, wherein at least one of said medium reservoir (22) and said medium dispensing and reservoir unit (15) is a component separate from said second housing body (5), said second housing body (5) including at least one reservoir retainer (18) for holding said medium dispensing and reservoir unit (15) against withdrawal from said second housing body (5), said second housing body (5) including a counter pressure face (9) facing in an opposite direction from said pressure faces (8) for manually actuating discharge of the media in response to pressure on opposite pressure faces (8,9).

21. The dispenser according to claim 18, including at least two separate medium dispensing and reservoir units (15, 15'), said second housing body (5) including reservoir retainers (18) for separately individually receiving said medium dispensing and reservoir units (15, 15') in substantially parallel juxtaposed orientations, said at least one outlet duct (37) including at least two separate outlet ducts (37) for separately receiving the media from said medium dispensing and reservoir units (15, 15'), said nozzle insert (35) being fixedly connected to said first housing body (4) and located entirely within said first housing body (4).

22. The dispenser according to claim 21, wherein in an axial view on said dispenser (1) said first and second housing bodies (4, 5) are oblong and include a body jacket (19), said cap jacket (33) axially over engaging said body jacket (19), thereby said cap jacket and said body jacket directly interengage with opposing circumferential faces to provide rotation prevention means for positively preventing rotation of said first housing body (4) with respect to said second housing body (5).

23. The dispenser according to claim 1, wherein at least one of said discharge orifices (7) penetrates an outlet wall (47) bounding said nozzle duct (49) in one part, in an axial view on said at least one discharge orifice (7) said outlet wall (47) being oblong, said downstream end section including two separate end sections (51) laterally juxtaposed and substantially abutting against said outlet wall (47).

24. The dispenser according to claim 23, wherein said outlet wall (47) defines a free end of a nozzle body (6) provided for insertion in a human body opening, said outlet wall (47) connecting to a jacket defining a nozzle body circumference (55), at said outlet wall (47) said nozzle body circumference (55) being oval and at a nozzle body location spaced upstream from said outlet wall (47) said nozzle body circumference (55) being substantially more evenly arcuated than at said outlet wall (47), said nozzle body circumference (55) substantially continuously changing from said outlet wall (47) to said stud location.

25. A dispenser (1) for discharging media comprising:

a housing body (4);

a medium delivery unit (23) including a pump;

a nozzle including a nozzle duct (49) with an upstream end and a downstream end including a final discharge orifice (7) for releasing at least one of the media from said dispenser (1) to an environment external to said dispenser (1), and a nozzle insert (35) inserted in said housing body (4) and including a core rod (41) extending substantially up to said upstream end of said nozzle duct (49), said core rod (41) defining an outer circumference, said nozzle insert (35) including a support member (45) directly connecting to an upstream end of said core rod (41), located entirely inside said housing body (4) and fixed to said housing body (4) laterally outside and spaced from said outer circumference of said core rod (41) with a support connector (46).

* * * * *